(12) United States Patent
Piferi et al.

(10) Patent No.: US 9,192,393 B2
(45) Date of Patent: Nov. 24, 2015

(54) MRI COMPATIBLE SURGICAL DRILLS AND RELATED METHODS

(71) Applicant: MRI Interventions, Inc., Memphis, TN (US)

(72) Inventors: Peter Piferi, Orange, CA (US); Daniele Ghidoli, Laguna Hills, CA (US)

(73) Assignee: MRI Interventions, Inc., Irvine, CA (US)

( * ) Notice: Subject to any disclaimer, the term of this patent is extended or adjusted under 35 U.S.C. 154(b) by 133 days.

(21) Appl. No.: 13/788,647

(22) Filed: Mar. 7, 2013

(65) Prior Publication Data
US 2013/0325012 A1 Dec. 5, 2013

Related U.S. Application Data

(60) Provisional application No. 61/653,695, filed on May 31, 2012.

(51) Int. Cl.
*A61B 17/16* (2006.01)

(52) U.S. Cl.
CPC ............. *A61B 17/16* (2013.01); *A61B 17/1624* (2013.01)

(58) Field of Classification Search
CPC ............... A61B 17/16; A61B 17/1613; A61B 17/1615; A61B 17/1617; A61B 17/1622; A61B 17/1624; B25B 17/00
USPC .......... 606/79–80, 96–98; 81/57.3, 57.29, 28, 81/34; 408/126, 234
See application file for complete search history.

(56) References Cited

U.S. PATENT DOCUMENTS

| | | | | |
|---|---|---|---|---|
| 1,508,282 | A | * | 9/1924 | Kenyon ............................. 81/34 |
| 1,732,613 | A | * | 10/1929 | Parsons ............................. 81/34 |
| 5,219,174 | A | * | 6/1993 | Zurbrugg et al. ............... 279/82 |
| 5,893,422 | A | * | 4/1999 | Huang .......................... 173/216 |
| 5,993,454 | A | | 11/1999 | Longo |
| 6,050,992 | A | | 4/2000 | Nichols |
| 6,167,311 | A | | 12/2000 | Rezai |
| 6,356,786 | B1 | | 3/2002 | Rezai et al. |

(Continued)

FOREIGN PATENT DOCUMENTS

| | | | |
|---|---|---|---|
| CN | 100341465 C | * | 10/2007 |
| WO | WO/2007064739 | | 6/2007 |
| WO | WO 2007/142830 A2 | | 12/2007 |

OTHER PUBLICATIONS

American Science & Surplus (online equipment catalog), 2013, www.sciplus.com/p/mini-hand-crank-drill_4101, Item # 92263P1 "Mini Hand Crank Drill".*

(Continued)

*Primary Examiner* — Anu Ramana
*Assistant Examiner* — Jessica Weiss
(74) *Attorney, Agent, or Firm* — Myers Bigel Sibley & Sajovec, P.A.

(57) ABSTRACT

A surgical, manually operated, hand-held MRI-compatible drill for drilling though target bone of a patient includes: a housing; a ring gear held in the housing; a hand crank attached to ring gear and the housing; a pinion gear held in the housing in cooperating alignment with the ring gear; an elongate shaft attached to the pinion on one end portion and to a chuck support on an opposing end portion; a chuck attached to the chuck support held; and jaws attached to the chuck support and residing in the chuck adapted to hold a drill bit. The drill is light-weight. The components can all be polymeric.

27 Claims, 9 Drawing Sheets

(56) References Cited

U.S. PATENT DOCUMENTS

| | | |
|---|---|---|
| 6,405,079 B1 | 6/2002 | Ansarinia |
| 6,438,423 B1 | 8/2002 | Rezai et al. |
| 6,526,318 B1 | 2/2003 | Ansarinia |
| 6,539,263 B1 | 3/2003 | Schiff et al. |
| 6,609,030 B1 | 8/2003 | Rezai et al. |
| 6,708,064 B2 | 3/2004 | Rezai |
| 6,716,215 B1 | 4/2004 | David et al. |
| 8,157,828 B2 | 4/2012 | Piferi |
| 8,175,677 B2 | 5/2012 | Sayler et al. |
| 2004/0003476 A1* | 1/2004 | Bierria et al. .............. 15/88 |
| 2004/0152968 A1 | 8/2004 | Iversen et al. |
| 2008/0177268 A1 | 7/2008 | Daum et al. |
| 2009/0099584 A1* | 4/2009 | Piferi .............. 606/180 |
| 2010/0034605 A1* | 2/2010 | Huckins et al. .............. 408/1 R |
| 2010/0185198 A1 | 7/2010 | Piferi et al. |
| 2010/0230926 A1* | 9/2010 | Dodman et al. .............. 280/276 |
| 2011/0066154 A1 | 3/2011 | Narducci et al. |

OTHER PUBLICATIONS

Notification of Transmittal of the International Search Report and the Written Opinion of the International Searching Authority, or the Declaration, PCT/US2013/041805, Date of Mailing: Aug. 21, 2013, 16 pages.

Helmut Kapczynski. *Surgical Instruments 101; An Introduction to KMedic Certified Instruments* (KMEDIC) Mar. 31, 2000, 181 pages.

\* cited by examiner

MRI COMPATIBLE SURGICAL DRILLS AND RELATED METHODS

RELATED APPLICATIONS

This application claims the benefit of and priority to U.S. Provisional Application Ser. No. 61/653,695, filed May 31, 2012, the contents of which are hereby incorporated by reference as if recited in full herein.

FIELD OF THE INVENTION

The present invention relates to medical devices and, more particularly, tools and methods for drilling in or through bone of a patient.

BACKGROUND OF THE INVENTION

During MRI-Guided surgeries, it can be desired to drill through bone such as a skull to define a surgical path for passing medical interventional devices.

SUMMARY OF THE INVENTION

Embodiments of the present invention are directed to a surgical, manually operated, hand-held drill that can be safely used in an MRI environment, including proximate the high-field magnet while a patient is on a bed/gantry of an MR Scanner.

Embodiments of the invention are directed to MRI-compatible hand-held, manually operable surgical drills. The drills include: a housing; a ring gear held in the housing; a hand crank attached to ring gear and the housing; a pinion gear held in the housing in cooperating alignment with the ring gear; a chuck extending from the housing; and jaws residing in the chuck adapted to hold a drill bit. The drill is light-weight.

The housing, ring gear, hand crank, pinion gear and chuck can be polymeric members.

The ring gear and hand crank can be provided as a unitary monolithic molded polymeric body.

The housing can have a circular portion that merges into an elongate portion. The ring and pinion gears can be held in the circular portion of the housing and the hand crank can be attached to one side of the circular portion of the housing.

The drill may include an elongate polymeric shaft that can be held in the elongate portion of the housing. The elongate shaft can be attached to the pinion on one end portion and to a chuck support on an opposing end portion.

The chuck can reside outside but proximate an end of the elongate portion of the housing.

The jaws can be polymeric jaws configured to releasably hold a respective drill bit having sizes between about 2.0 mm to about 3.2 mm.

The ring and pinion gears can have a gear ratio of 3:1.

The drill can be compact and can have a length that is less than 7 inches and a maximum width dimension that is less than four inches.

The hand crank can have a lever with a knob that together has a length that extends beyond the housing about 1-3 inches. The lever with knob can have an outer travel diameter of between about 5-7 inches.

The circular portion of the housing can have a diameter of about 3 inches.

The ring and pinion gears can be acetal gears.

The shaft, chuck jaws and chuck support can be Polyetheretherketone (PEEK) components.

Other embodiments are directed to surgical kits for an MRI-guided interventional surgery on a patient. The kits include a sterile manually operated, light weight, hand-held surgical drill and sterile packaging containing the drill. The drill can include a polymeric housing; a polymeric ring gear held in the housing; a polymeric hand crank attached to the ring gear and the housing; a polymeric pinion gear held in the housing in cooperating alignment with the ring gear; a polymeric chuck extending from the housing; and jaws residing in the chuck adapted to hold a drill bit.

The kit may include a plurality of drill bits configured to be releasably held by the jaws of the drill.

Yet other embodiments are directed to methods of forming an aperture in bone of a patient during an MRI guided surgical procedure. The methods include: (a) placing a patient on a gantry in an MR Scanner room; (b) holding a hand-held drill with a hand-crank against a target location of a patient while the patient is on the gantry; (c) manually rotating the hand crank; and (d) forming an aperture in target bone of the patient in response to the rotating step.

Further features, advantages and details of the present invention will be appreciated by those of ordinary skill in the art from a reading of the figures and the detailed description of the preferred embodiments that follow, such description being merely illustrative of the present invention.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

DETAILED DESCRIPTION OF EMBODIMENTS OF THE INVENTION

The present invention now will be described more fully hereinafter with reference to the accompanying drawings, in which illustrative embodiments of the invention are shown. In the drawings, the relative sizes of regions or features may be exaggerated for clarity. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90° or at other orientations) and the spatially relative descriptors used herein interpreted accordingly. The term "about" refers to numbers in a range of +/−20% of the noted value.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

The term "light-weight" refers to drills that weigh less than 1 pound. The term "MRI compatible" means that the so-called component(s) are safe for use in an MRI environment (e.g., in a high magnetic field of an MRI scanner) and are typically made of non-ferromagnetic MRI compatible material(s) suitable to reside and/or operate in a higher magnetic field environment. The term "high magnetic field" refers to field strengths above about 0.5 T, typically between 1.5 T and 10 T, e.g., typically 1.5 T, 2 T, 3 T, associated with MRI/MR Scanners. The term "gantry" refers to a patient support of an MRI scanner and may include the patient table or other structure.

The terms "MRI or MR Scanner" (or MRI/MR scanner) are used interchangeably to refer to a Magnetic Resonance Imaging system and includes the magnet, the operating components, e.g., RF amplifier, gradient amplifiers and operational circuitry including, for example, processors (the latter of which may be held in a control cabinet) that direct the pulse sequences, select the scan planes and obtain MR data.

The term "RF safe" means that the device is configured to operate safely when exposed to RF signals, particularly RF signals associated with MRI systems, without inducing unplanned current that inadvertently unduly heats local tissue or interferes with the planned therapy.

The term "sterile" means that the device meets or exceeds surgical cleanliness standards.

According to embodiments of the present invention, surgical drills and methods for using the same are provided for forming a surgical entry path into or through bone of a patient. According to some embodiments, the drills and methods are used or usable to form an access path through a patient's skull. Such marking may be employed to indicate to a physician a designated location for entry into the patient (for example, through the patient's skull).

With reference to FIGS. 1-6, an MRI-compatible, hand-held surgical drill 10 according to embodiments of the present invention is shown therein. The drill 10 is compact and light weight. All drill components can be of MRI compatible materials, typically non-metallic materials. The drill bit can be of non-ferromagnetic metal. In some embodiments, most if not all of the drill components are substantially rigid polymeric members. The drill 10 (without any drill bit loaded therein) can typically weigh between about 0.5 pounds to about 1 pound, and in some particular embodiments can be about 6 ounces (sans the drill bit). The jaws 50 may be metallic such as titanium or stainless steel, but are typically polymeric with grip strength sufficient to hold the drill bit (in cooperation with the chuck 55).

Figure 4:
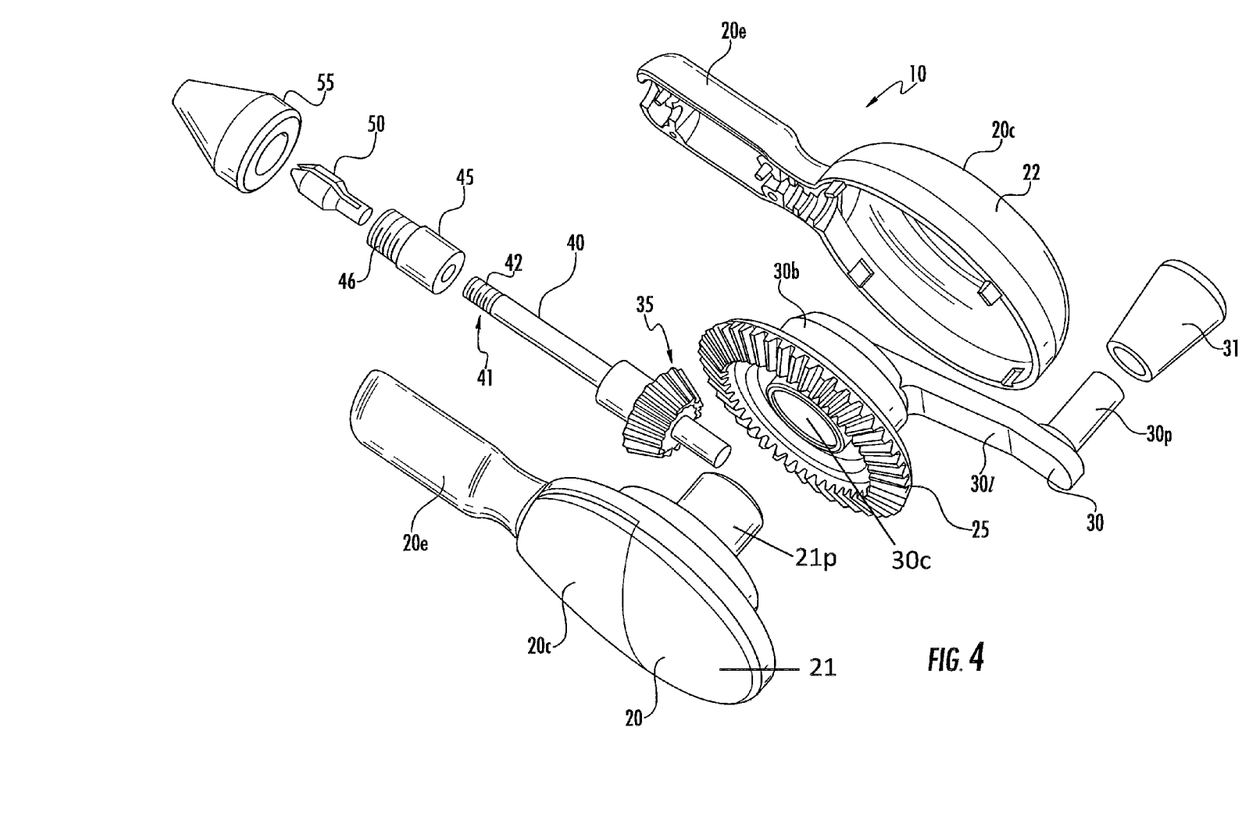
FIG. 4 is an exploded view of the device shown in FIG. 1.
Figure 5:
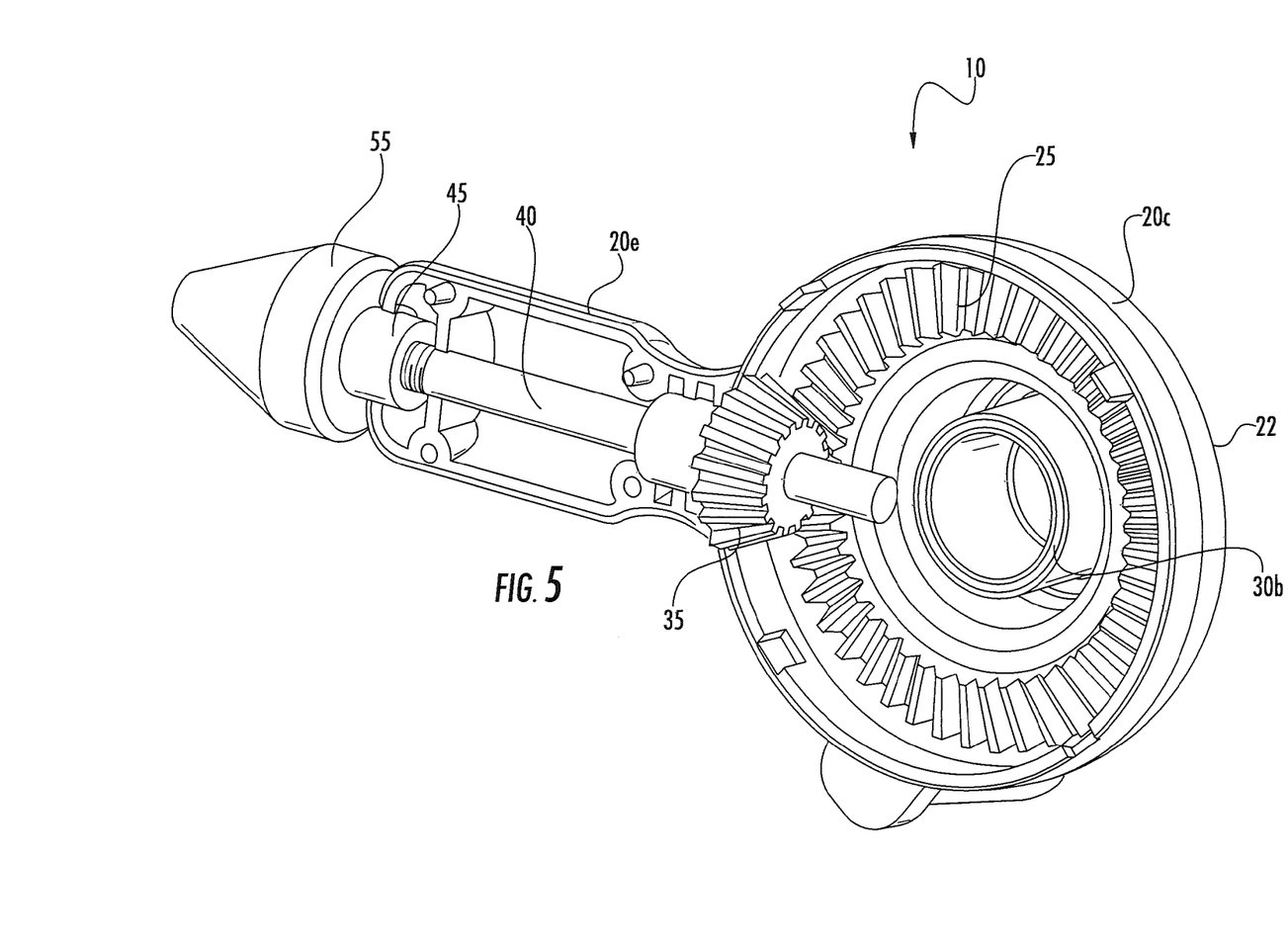
FIG. 5 is a side, perspective view on a portion of the drill shown in FIG. 1 illustrating the gear engagement according to embodiments of the present invention.
Figure 6:
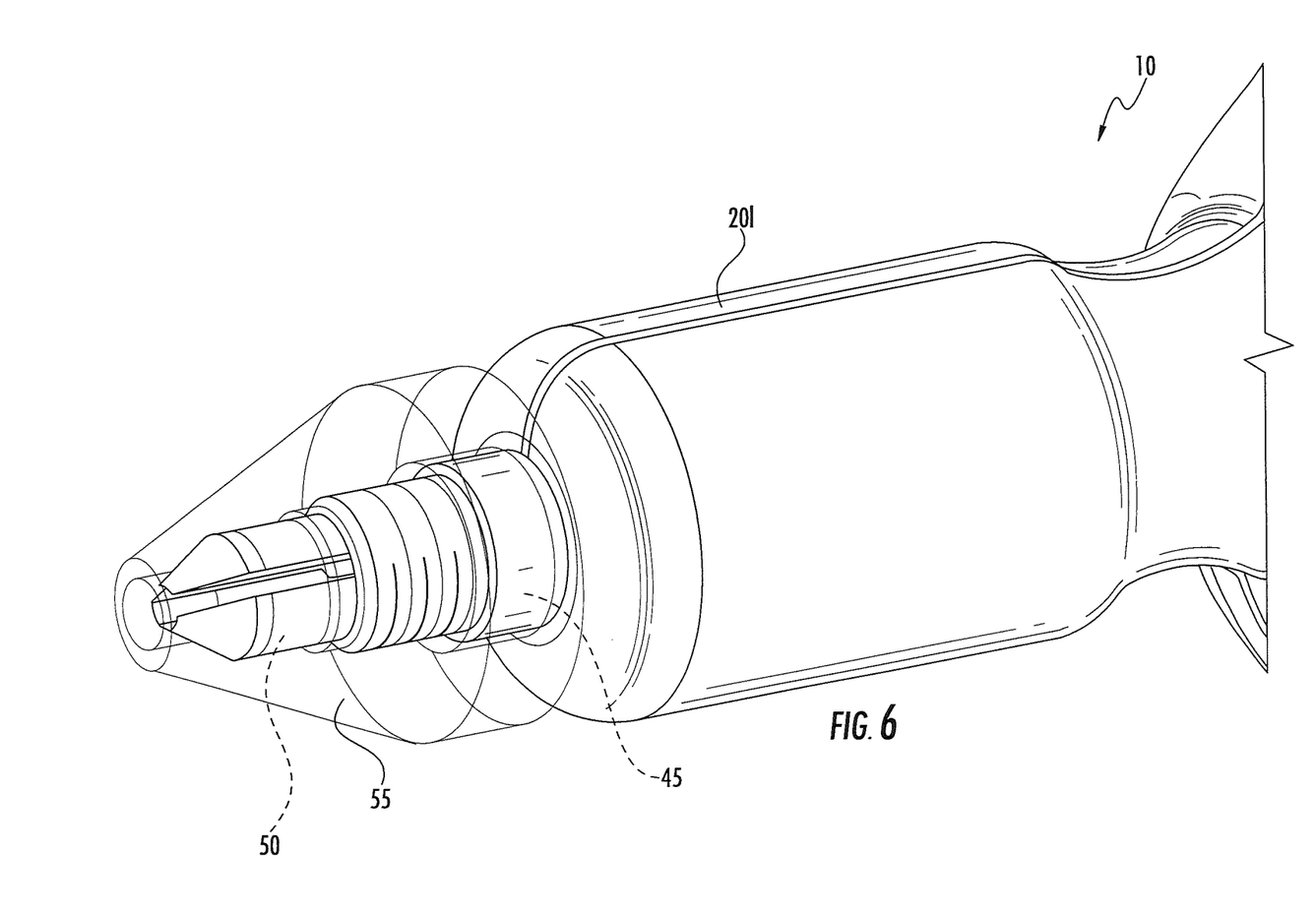
FIG. 6 is a perspective, enlarged view of the end of the drill shown in FIG. 1 with the chuck shown transparent to illustrate the encased components according to embodiments of the present invention.

The drill 10 includes a housing body 20 with first and second housings 21, 22, that matably engage to enclose a ring gear 25 therebetween. A rotatable hand crank 30 with a knob 31 is attached to the ring gear 25. The drill 10 includes a pinion gear 35 that engages the ring gear 25. The pinion gear 35 can be attached to elongate shaft 40. A distal end 41 of the elongate shaft 40 can be threaded 42 and is attached to chuck support 45. The distal end portion of the chuck support 46 has external threads that attaches to chuck 55. Jaws 50 resides inside the distal end 46 of the chuck support and inside the chuck 55 (FIG. 6).

In other embodiments, the drill can have a different internal assembly which does not require the elongate shaft. That is, the pinion gear 35 may also be attached to a different component to provide the rotational motion to a drill bit.

The housing 20 can include a substantially circular portion 20c that holds the crank 30 and an elongate portion 20e that holds the shaft 40. The elongate portion 20e can have a length that is similar to the length or the circular portion, each at between about 2.5-3.5 inches. Although not shown, the drill can omit the elongate portion 20e. However, it is contemplated that use of the elongate housing shape may promote hygienic use and/or sterility.

Figure 1:
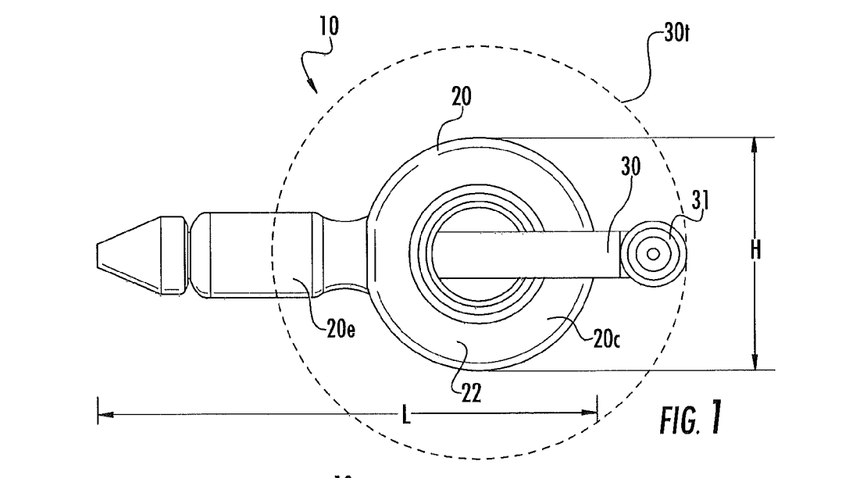
FIG. 1 is a side view of an MRI compatible hand-held, manually operated surgical drill according to embodiments of the present invention.
Figure 2:
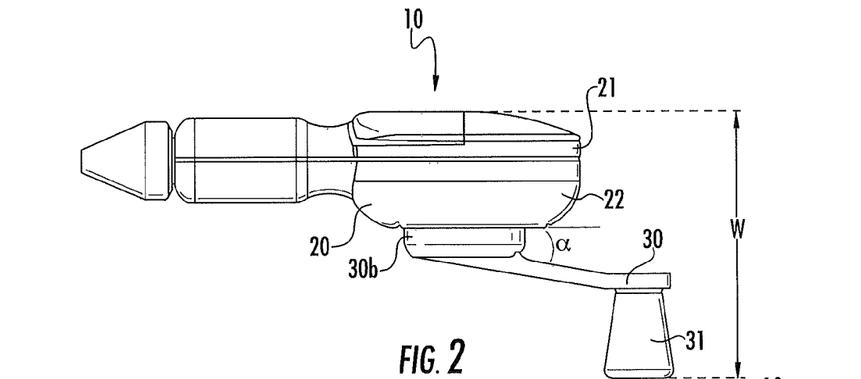
FIG. 2 is a top view of the device shown in FIG. 1.
Figure 3:
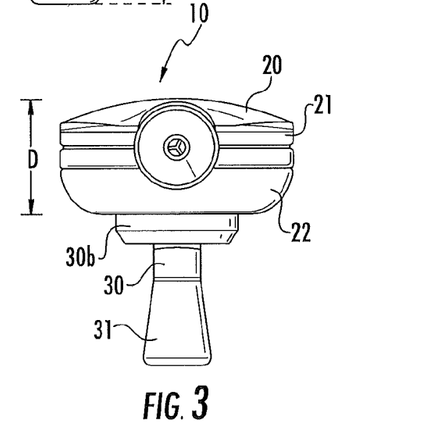
FIG. 3 is an end view of the device shown in FIG. 1.

Referring to FIG. 2, the hand crank 30 can extend away from the housing body 20b at an angle "α" that is between about 8-15 degrees, typically about 9 degrees from a plane extending through the interface of the hand crank adjacent the housing 20. The hand crank (lever) 30 can have a length that is about 2.5-4 inches and the knob can have a length that is about 1-1.25 inches. Typically, the hand crank 30 has a length that is about 2.7 inches. Referring to FIGS. 2 and 4, the hand crank 30 can have a base 30b that extends into the housing 22 and is attached to the ring gear 25. Thus, the base 30b can rotate relative to the housing 22. The internal portion of the base 30b can have a cavity 30c that is aligned with a projecting post 21p from the opposing housing 21. The hand crank 30 can have a lever 30l with and end portion with a post 30p that holds the knob 31. The lever 30l with knob 31 can have a length that extends beyond the housing about 1-3 inches. The lever 30l with knob 31 can have an outer travel diameter 30t of between about 5-7 inches (indicated by broken line perimeter circle in FIG. 1).

The chuck 55 can be used with a range of different (diameter and length) size drill bits 260 (FIG. 9) including between about 2.0 mm to about 3.2 mm. This may allow for one drill to be used to make different size openings that may be desired for a procedure, such as for pins, bone screws and/or burr holes and the like.

Figure 11:
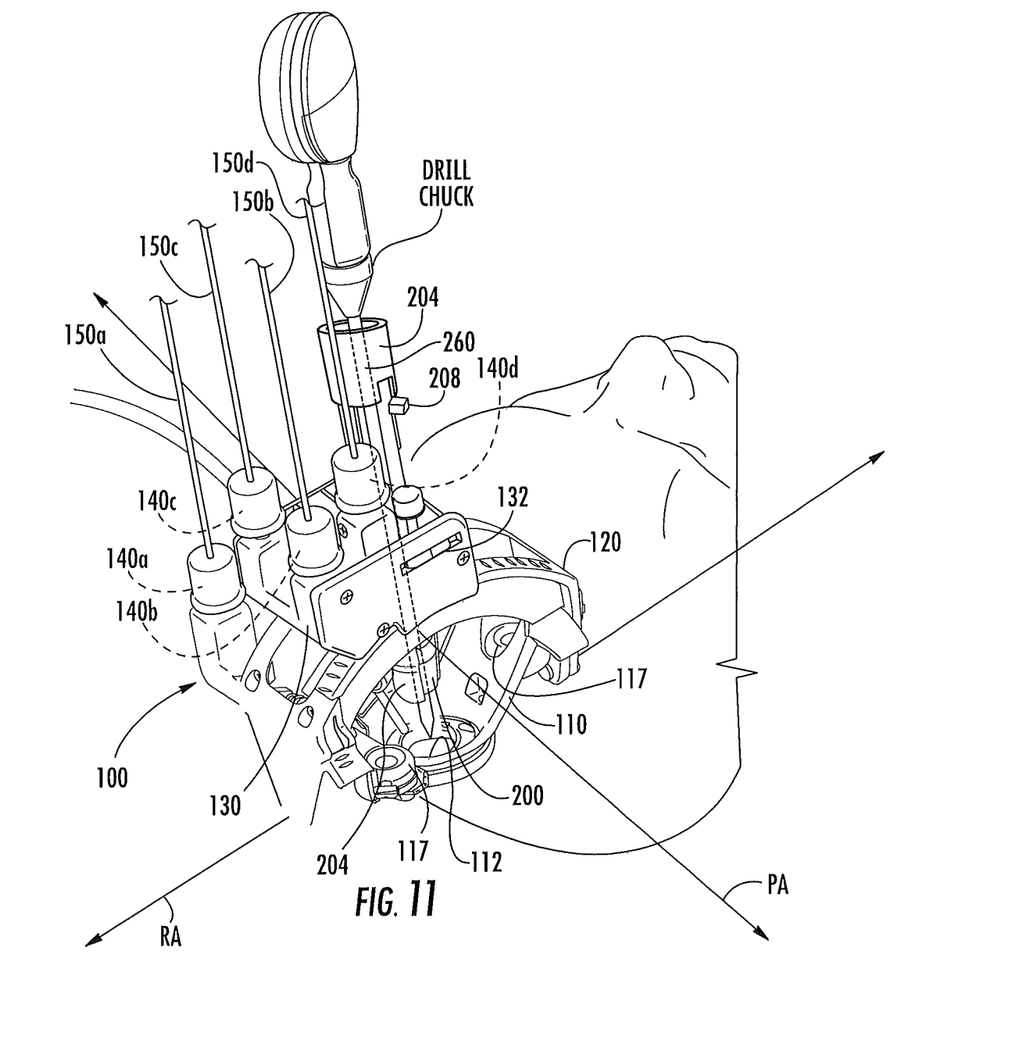
FIG. 11 is a front perspective view of a targeting cannula through which the drill bit held by the drill can be extended during a drilling operation according to some particular embodiments of the present invention.

In some embodiment, the drill bits 260 can be provided in a plurality of different lengths, such as length, typically about 2 cm up to about 22 cm. For the latter, the long drills can be used with the drill bit 260 extending through a targeting cannula 204. Examples of targeting cannulas 204 are described in U.S. Patent Application Publication 2009/0112084 and as shown in FIG. 11). The content of this document is incorporated by reference as if recited in full herein.

The drill 10 can be economic (relatively low cost) and sterile (and packaged in sterile packaging) allowing for a single-use disposable configuration rather than a re-usable product.

The ring gear 25 and the pinion gear 35 can be molded acetal or other suitable polymeric material. The gear ratio can be 2:1, 3:1, 4:1, 5:1, or 6:1, but is typically about 3:1.

The hand crank 30, e.g., body 30b and lever 30l can be molded as one piece with the ring gear 25 and be the same (molded) material such as acetal.

In operation, a user turns the hand crank 30 which rotates about an axis in a travel path 30t (FIG. 1) that has an outer perimeter diameter of between about 3-6 inches, typically about 5.36 inches. The hand crank 30 rotates the ring gear 25 which turns the pinion gear 35, which turns the chuck support 45 with jaws 50 that rotates the drill bit (when attached).

Excluding the hand crank 30, the drill 10 can have a height dimension "H" that is about three inches, a length "L" that is about 6.5 inches, and a depth "D" that is about 2 inches. With the hand crank, the depth dimension can be a width dimension "W" that is less than the length dimension L, typically between about 3-5 inches, such as about 3.5 inches, about 4 inches or about 4.5 inches.

Table I below provides exemplary materials for different components of the drill according to particular embodiments of the present invention. However, other polymeric materials may also be used, for example, ABS or polycarbonate. PEEK refers to Polyetheretherketone.

TABLE 1

MATERIAL EXAMPLES

| Description | Material | Process |
|---|---|---|
| Main Gear Support | Nylon | Molded |
| Main Gear | Acetal | Molded |
| Pinion | Acetal | Molded |
| Main Gear Housing | Nylon | Molded |
| Shaft | Peek | Machined |
| Knob | Nylon | Molded |
| Chuck Support | Peek | Machined |
| Jaws | Peek | Machined |
| Chuck | Peek | Machined |

Figure 7:
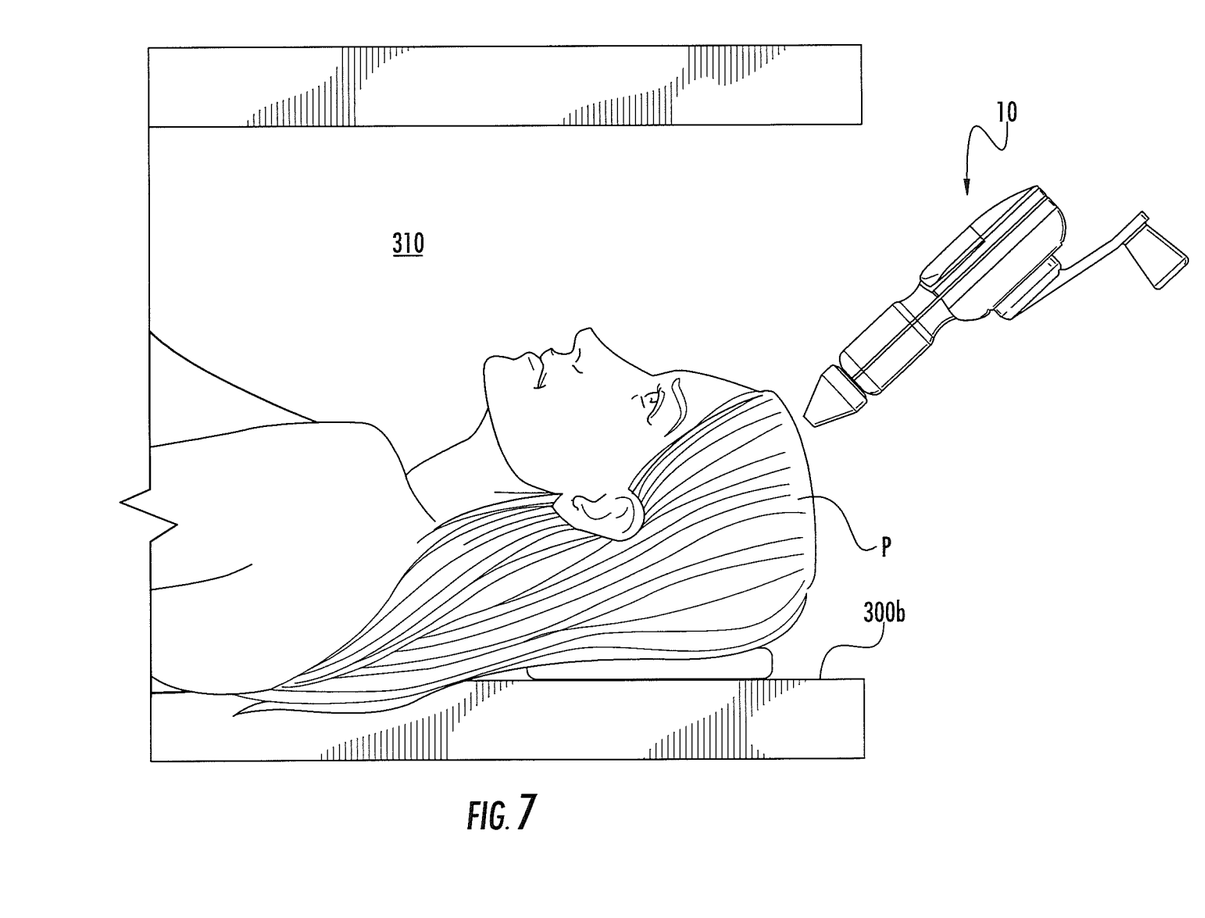
FIG. 7 is a schematic illustration of a patient residing in an MR Scanner during a surgical procedure according to embodiments of the present invention.

Exemplary use of the drill 10 and methods according to embodiments of the present invention will be further described with reference to FIGS. 7, 8A and 8B. Referring to FIG. 7, a portion of a patient's head "P" is shown therein. The head includes an outer skin (and other soft tissue) layer (referred to herein as the scalp), a skull, and underlying brain tissue. The skull includes an outer compact bone layer, an inner compact bone layer, and a spongy bone layer between the compact bone layers. According to some embodiments, the drilling can occur with the patient's head in or adjacent a bore 310 of a high-field magnet of an MRI scanner 300 as shown in FIG. 7 (can be open bore or closed bore magnets). The patient "P" can be on an MR Scanner gantry or bed 300b.

Figure 8A:
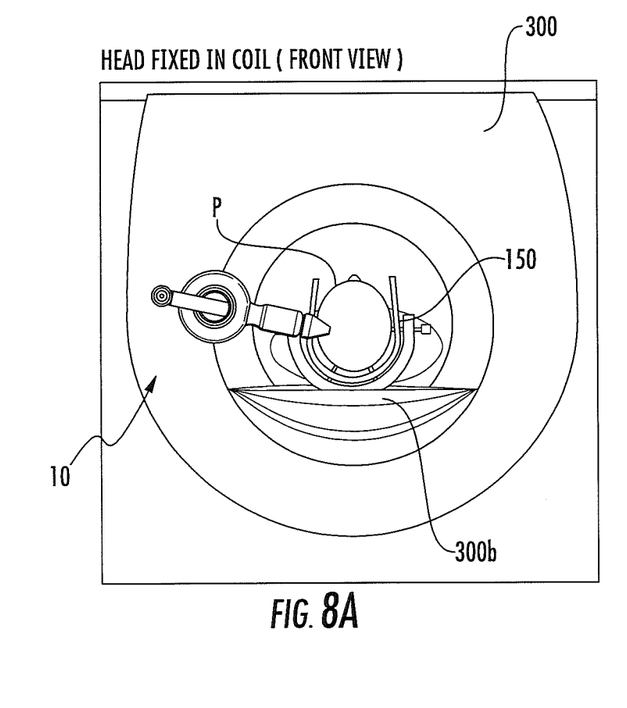
FIGS. 8A and 8B are schematic illustrations of a patient in a head fixation frame according to embodiments of the present invention.
Figure 8B:
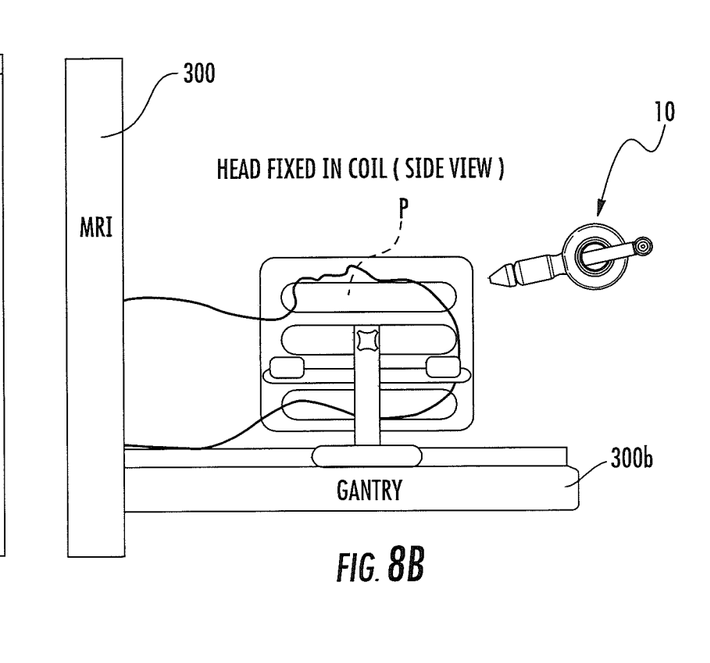

Typically, as shown in FIGS. 8A and 8B, the patient's head is in a head fixation assembly 150 that may include head coils and typically includes one or more head restraints including a belt and bone screws to inhibit patient movement during surgery. See, e.g., U.S. patent application Ser. No. 12/685,849, the contents of which are hereby incorporated by reference as if recited in full herein. The head fixation assembly 150 can have any suitable configuration and the embodiment shown is by way of example only.

FIG. 8A illustrates that the drilling may occur while the patient is fully retracted in the bore 310 of the magnet of the MR Scanner 300. FIG. 8B illustrates that the gantry may be extended a distance outside the bore during use of the drill 10.

Figure 9:
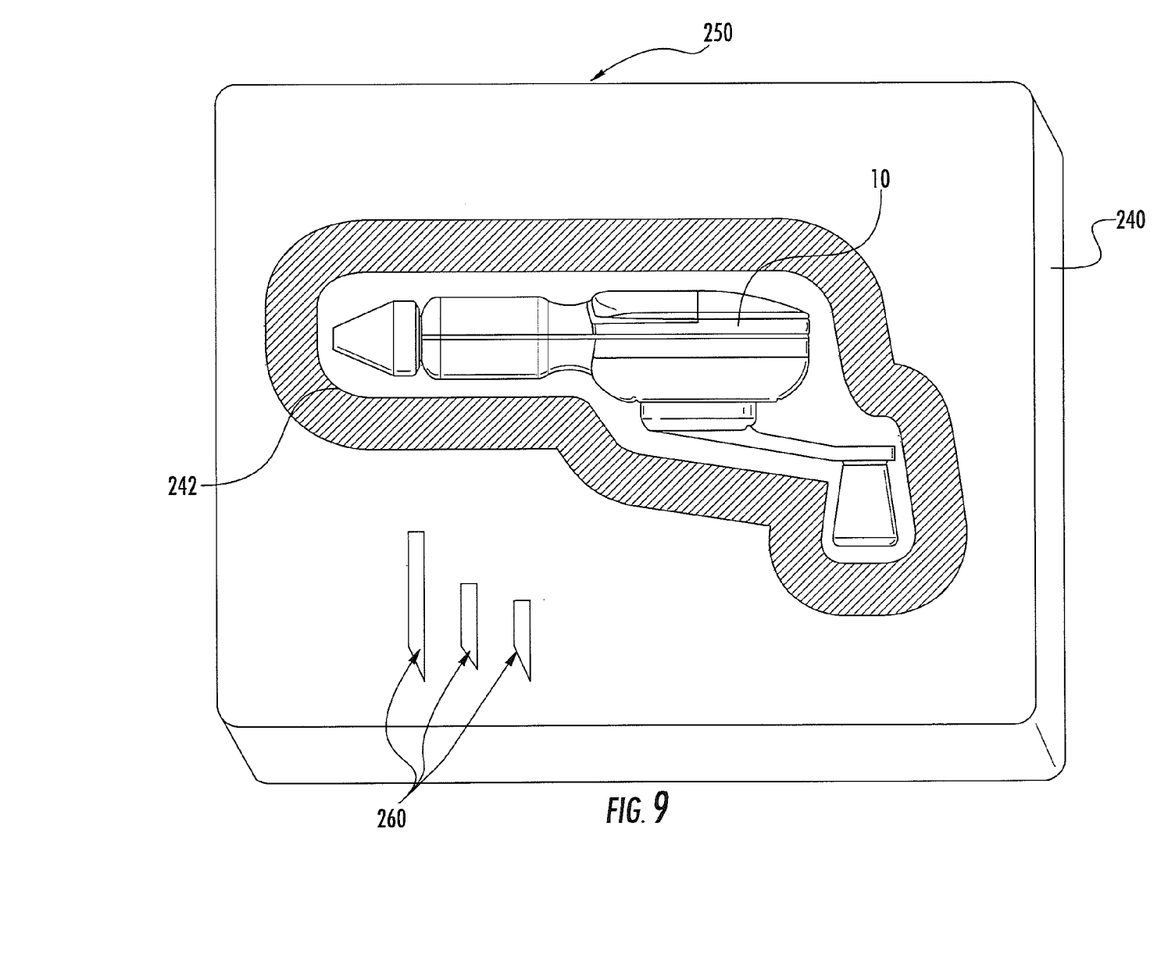
FIG. 9 is a view of a medical kit including the drill of FIG. 1.

According to some embodiments and as shown in FIG. 9, the drill 10 is packaged in sterile packaging 240 to provide a medical kit 250. The packaging 240 may include a cavity with foam or other snug compartment that holds the drill 10 and protects it from shipping and handling damage. The kit 250 can include inner packaging (e.g., a semi-rigid and/or vacuum formed polymeric packaging) and an outer packaging (e.g., a loose, breathable polymeric bag). According to some embodiments, the kit 250 includes one or more biocompatible, MR compatible drill bits 260, which may be in different sizes. The drill bits may, for example, be non-ferromagnetic metal such as stainless steel or titanium and the like or may be of other sufficient rigid material.

Figure 10:
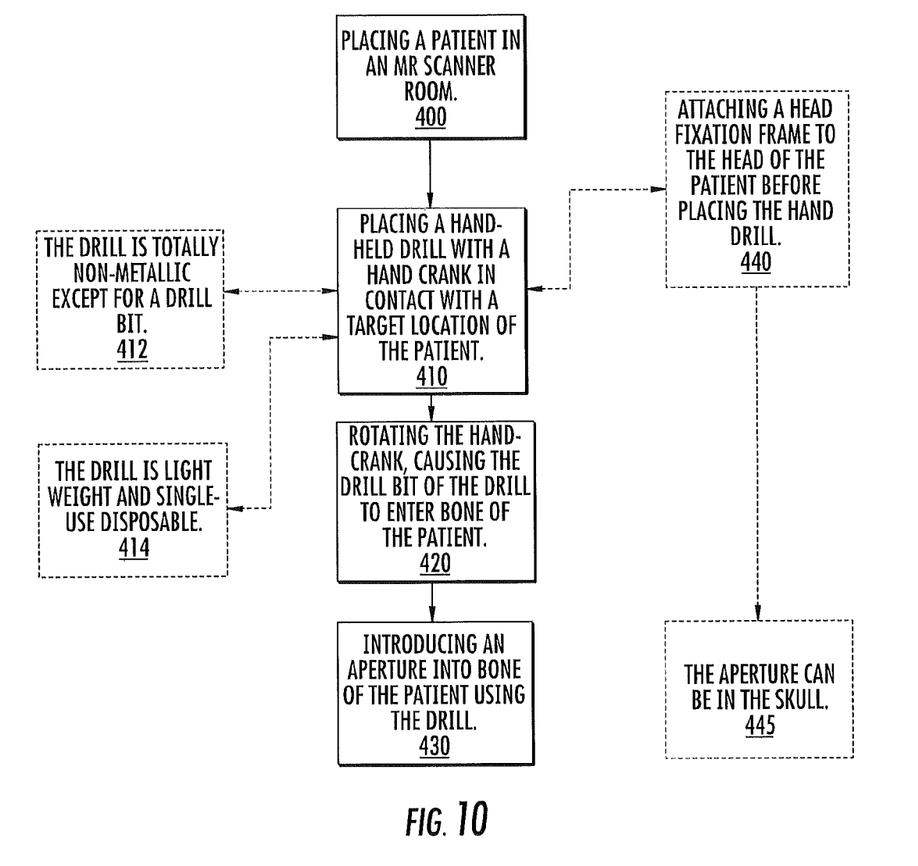
FIG. 10 is a flow chart of exemplary operations that can be used to form an aperture in target bone of a patient according to embodiments of the present invention.

FIG. 10 illustrates exemplary operations that can be used to carry out embodiments of the invention. A patient is placed in an MRI scanner room (block 400). The patient can be placed on a gantry for retraction into the Scanner bore. A hand-held drill with a hand crank is placed in contact with a target location of the patient (block 410). A user rotates the hand-crank, causing the drill bit of the drill to enter bone of the patient (block 420). An aperture is introduced into bone of the patient using the dill (block 430).

Optionally, a head fixation frame can be attached to the head of the patient before placing the hand drill (block 440). The aperture can be in the skull (445).

The drill can be totally non-metallic except for a drill bit (block 412). The drill can be light weight and single-use disposable (block 414).

In some embodiments, the drill 10 and methods form a part of or operate with MRI compatible interventional systems. The drill can be provided with a set of interventional tools for a particular procedure type. In some embodiments, the MRI compatible interventional systems include the drill 10 with trajectory guide systems and/or apparatus and related components and methods. According to some embodiments, the trajectory guide apparatus and methods are frameless stereotactic trajectory guide apparatus that may be particularly suitable for deep brain interventional procedures, but may be used in other target anatomical locations as well.

Some-embodiments of the invention are directed to MRI interventional procedures and provide interventional tools and/or therapies that may be used to locally place surgical interventional objects, tools or therapies in vivo to site specific regions using an MRI system. The interventional tools can be used to define an MRI-guided trajectory or access path to an in vivo treatment site.

In some embodiments, MRI can be used to visualize (and/or locate) a therapeutic region of interest inside the brain and utilize an MRI to visualize (and/or locate) an interventional tool or tools that will be used to deliver therapy and/or to place a permanently implanted device that will deliver therapy. Then, using the imaging data produced by the MRI system regarding the location of the therapeutic region of interest and the location of the interventional tool, the system and/or physician can make positional adjustments to the interventional tool so as to align the trajectory of the interventional tool, so that when inserted into the body, the trajectory of the interventional tool will intersect with the therapeutic region of interest. With interventional tool now aligned with the therapeutic region of interest, an interventional probe can be advanced, such as through an open lumen inside of the interventional tool, so that the interventional probe follows the trajectory of the interventional tool and proceeds to the therapeutic region of interest. The interventional tool and the interventional probe may or may not be part of the same component or structure.

Tools, methods and systems in accordance with the present invention may be used with apparatus and methods as described in one or more of the following patent applications: U.S. Provisional Patent Application No. 60/933,641, filed Jun. 7, 2007; U.S. Provisional Patent Application No. 60/974, 821, filed Sep. 24, 2007; and PCT Application No. PCT/US2006/045752, published as PCT Publication No. WO/2007064739 A2, and U.S. patent application Ser. No. 12/134,412, filed Jun. 6, 2008, the disclosures of which are hereby incorporated by reference.

According to some embodiments, instrumentation and equipment are inserted through a targeting cannula to execute a diagnostic and/or surgical procedure. According to some embodiments, the procedure includes a deep brain stimulation procedure wherein one or more electrical leads are implanted in a patient's brain. The apparatus described herein can serve to designate an entry point into a patient for an established trajectory for installing the lead or leads or other interventional devices such as, for example, but not limited to, ablation probes, injection catheters and the like.

Some embodiments can be configured to deliver tools or therapies that stimulate a desired region of the sympathetic nerve chain. Other uses inside or outside the brain include stem cell placement, gene therapy or drug delivery for treating conditions, diseases, disorders or the like. Some embodiments can be used to treat tumors.

Some embodiments can be used with systems to deliver bions, stem cells or other target cells to site-specific regions in the body, such as neurological target and the like. In some embodiments, the systems deliver stem cells and/or other cardio-rebuilding cells or products into cardiac tissue, such as a heart wall via a minimally invasive MRI guided procedure, while the heart is beating (i.e., not requiring a non-beating heart with the patient on a heart-lung machine). Examples of known stimulation treatments and/or target body regions are described in U.S. Pat. Nos. 6,708,064; 6,438,423; 6,356,786; 6,526,318; 6,405,079; 6,167,311; 6539,263; 6,609,030 and 6,050,992, the contents of which are hereby incorporated by reference as if recited in full herein.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention. Therefore, it is to be understood that the foregoing is illustrative of the present invention and is not to be construed as limited to the specific embodiments disclosed, and that modifications to the disclosed embodiments, as well as other embodiments, are intended to be included within the scope of the invention.

That which is claimed is:

1. An MRI compatible hand-held, manually operable surgical drill, comprising:
    a housing;
    a ring gear held in the housing;
    a hand crank attached to the ring gear, wherein the hand crank has an elongate lever that merges into a base, wherein the base of the hand crank has an internal portion that is surrounded by the ring gear, and wherein the lever resides outside the housing while the internal portion of the base is held in the housing;
    a pinion gear held in the housing in cooperating alignment with the ring gear;
    a chuck extending from the housing; and
    jaws attached to a chuck support and residing in the chuck adapted to hold a drill bit so that the drill bit extends out from the chuck,
    wherein the drill is sterile for surgical use and light-weight, wherein the housing comprises first and second housing members that attach together to enclose the ring and pinion gear and the internal portion of the base of the hand crank, wherein each of the first and second housing members have an exterior wall with a circular portion having a circular outer perimeter extending about a centerline that is in line with an axis of rotation of the ring gear, wherein the axis of rotation is perpendicular to a longitudinally extending centerline of the chuck, wherein the circular portion of the first housing member holds the ring gear and the internal portion of the base of the hand crank, wherein the ring gear surrounds a cylindrical internal wall of the internal portion of the base of the hand crank that extends about an inwardly facing cylindrical cavity, wherein the circular portion of the second housing member comprises an internal, inwardly projecting member that extends a distance into the cylindrical cavity, and wherein the ring gear, the hand crank lever and the hand crank base are a unitary single polymeric molded member.

2. The drill of claim 1, wherein the housing and pinion gear are polymeric.

3. The drill of claim 2, wherein the housing circular portion merges into an elongate portion, wherein the ring and pinion gears are held totally enclosed in the circular portion of the housing, wherein the hand crank base has a circular external portion that extends out of the first housing and that merges into the lever, and wherein the lever angles outward from the housing at an angle of between 8-15 degrees.

4. The drill of claim 3, wherein the circular portion of the housing has a diameter of about 3 inches, and wherein the circular portion of the external portion of the base of the hand crank is less than 3 inches.

5. The drill of claim 3, wherein the drill further comprising an elongate polymeric shaft that is held in the elongate portion of the housing that is attached to the pinion on one end portion and the chuck support on an opposing end portion, and wherein the chuck resides outside but proximate an end of the elongate portion of the housing.

6. The drill of claim 1, wherein the cylindrical internal wall is adjacent to, but spaced apart from, the ring gear, and wherein the cylindrical wall resides below the ring gear when the ring gear is held facing upward.

7. The drill of claim 1, wherein all components of the drill are polymeric.

8. The drill of claim 1, wherein the jaws are polymeric jaws configured to releasably hold a respective drill bit having sizes between about 2.0 mm to about 3.2 mm.

9. The drill of claim 1, wherein the ring and pinion gears have a gear ratio of 3:1.

10. The drill of claim 1, wherein the drill is compact and has a length that is less than 7 inches and a maximum width dimension that is less than four inches.

11. The drill of claim 1, wherein the lever has an outer end portion with a knob that together has a length that extends beyond the housing about 1-3 inches, wherein the lever with knob has an outer travel diameter of between about 5-7 inches, and wherein a maximal width dimension of the drill is between 3-5 inches.

12. The drill of claim 1, wherein the ring and pinion gears are acetal gears.

13. The drill of claim 1, wherein the chuck, jaws and chuck support are Polyetheretherketone (PEEK) components.

14. The drill of claim 1, wherein the first and second housing members have only a single elongate portion that extends off the circular portion, wherein the single elongate portion extends in a direction toward the jaws, and wherein a maximal width dimension of the drill is between 3-5 inches.

15. The drill of claim 1, wherein the base of the hand crank has an external portion held by the first housing member and has an internal portion that defines the cylindrical wall with the cylindrical cavity.

16. An MRI compatible hand-held, manually operable surgical drill, comprising:
a housing comprising first and second housing members that attach together to define an enclosed cavity, wherein each of the first and second housing members have a circular portion that merges into an elongate portion, wherein the circular portion of each of the first and second housing members has a circular outer perimeter extending about a centerline that projects across the first and second housing members that is perpendicular to a longitudinally extending centerline of the elongate portion;
a ring gear held in the housing;
a hand crank attached to the ring gear and the housing;
a pinion gear held in the housing in cooperating alignment with the ring gear;
a chuck extending from the elongate portion of the housing; and
jaws attached to a chuck support and residing in the chuck adapted to hold a drill bit so that the drill bit extends out from the chuck,
wherein the drill is sterile for surgical use and light-weight, wherein the housing, ring gear, pinion gear and hand crank are polymeric, wherein the hand crank and ring gear are a unitary monolithic molded body, and wherein the circular portion of the second housing member comprises an internal cylindrical projecting member that extends a distance into an aligned upwardly or downwardly facing cylindrical cavity that is surrounded by the ring gear, the cylindrical cavity bounded by an internal cylindrical wall held by the circular portion of the first housing member that faces upwardly or downwardly in the same direction as the cylindrical cavity.

17. The drill of claim 16, wherein the hand crank has an elongate lever that merges into a base, wherein the base of the hand crank has opposing cylindrical external and internal portions, the internal portion residing in an open space inside a perimeter of the ring gear and defining the cylindrical wall and cylindrical cavity, wherein the external base portion and lever reside outside the housing while the internal portion of the base is held in the housing.

18. The drill of claim 17, wherein the second housing member holds an integrally molded polymeric projecting member as the cylindrical projecting member, wherein the ring gear, the hand crank lever and the hand crank base are a unitary single polymeric molded member, and wherein a maximal width dimension of the drill is between 3-5 inches.

19. A surgical kit for an MRI-guided interventional surgery on a patient, the kit comprising:
a sterile manually operated, light weight, hand-held surgical drill, comprising:
a polymeric housing;
a polymeric ring gear held in the housing;
a polymeric hand crank attached to ring gear;
a polymeric pinion gear held in the housing in cooperating alignment with the ring gear;
a polymeric chuck extending out of the housing;
jaws residing in the chuck adapted to hold a drill bit; and
at least one package holding the surgical drill,
wherein the polymeric housing includes first and second housing members, wherein the first and second housing members have an exterior circular portion with a circular outer perimeter extending about a centerline in line with an axis of rotation of the ring gear that is perpendicular to a longitudinally extending centerline of the chuck, wherein the circular portion of the first housing member holds the ring gear and the hand crank, wherein the circular portion of the second housing member comprises a projecting member that extends a distance into an aligned upwardly or downwardly facing cylindrical cavity that is surrounded by the ring gear, the cylindrical cavity bounded by a cylindrical wall that faces upwardly or downwardly in the same direction as the cylindrical cavity, wherein the ring gear, the hand crank lever and the hand crank base are a unitary single polymeric molded member.

20. The kit of claim 19, further comprising a plurality of drill bits configured to be releasably held by the jaws of the drill in the at least one package.

21. The kit of claim 20, wherein the projecting member is cylindrical and faces into the cylindrical cavity.

22. The kit of claim 19, wherein the cylindrical internal wall is adjacent to, but spaced apart from, the ring gear and resides below gear teeth of the ring gear, when the ring gear is held facing upward.

23. The kit of claim 19, wherein the drill further comprises an elongate polymeric shaft attached to the pinion on one end portion and to a chuck support on an opposing end portion, and wherein the chuck is attached to the chuck support and resides outside the polymeric housing.

24. The kit of claim 19, wherein the first and second housing members have only a single elongate portion that extends off the circular portion, wherein the single elongate portion extends in a direction toward the jaws, and wherein a maximal width dimension of the drill is between 3-5 inches.

25. A method of forming an aperture in bone of a patient during an MRI guided surgical procedure, comprising:
   placing a patient on a gantry in an MR Scanner room;
   holding a hand-held drill with a hand crank against a target location of a patient while the patient is on the gantry, wherein the hand crank is attached or integral to a polymeric ring gear that is attached to a pinion gear, with both the ring gear and pinion gears held inside an enclosed housing of the hand-held drill;
   manually rotating a lever of the hand crank, wherein the lever merges into a base of the hand crank, wherein the base of the hand crank has opposing external and internal portions, wherein the internal portion is surrounded by the ring gear and held inside the enclosed housing, and wherein the lever and the external portion of the base reside outside the enclosed housing; and
   forming an aperture in target bone of the patient in response to the rotating step.

26. The method of claim 25, wherein the drill comprises polymeric ring and pinion gears held inside a polymeric housing.

27. A method of forming an aperture in bone of a patient during an MRI guided surgical procedure, comprising:
   placing a patient on a gantry in an MR Scanner room;
   holding a hand-held drill with a hand crank and ring and pinion gears against a target location of a patient while the patient is on the gantry, wherein the hand crank is attached or integral to a polymeric ring gear that is attached to a pinion gear, with both the ring gear and pinion gears held inside an enclosed housing of the hand-held drill;
   manually rotating the hand crank, wherein the hand crank has a lever that merges into a base of the hand crank, wherein the base of the hand crank has opposing external and internal portions, wherein the internal portion is surrounded by the ring gear and held inside an enclosed housing, and wherein the lever and the external portion of the base reside outside the enclosed housing; and
   forming an aperture in target bone of the patient in response to the rotating step; and
   directing a drill bit held by the drill through an elongate targeting cannula, then into the patient for the rotating and forming steps.

\* \* \* \* \*